United States Patent
Lee (10) Patent No.: US 9,687,560 B2
(45) Date of Patent: Jun. 27, 2017

(54) SKIN-PERMEATING PEPTIDE

(71) Applicant: LG Household & Health Care Ltd., Seoul (KR)

(72) Inventor: Seol Hoon Lee, Daejeon (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 92 days.

(21) Appl. No.: 14/404,928

(22) PCT Filed: May 31, 2013

(86) PCT No.: PCT/KR2013/004849
§ 371 (c)(1),
(2) Date: Dec. 1, 2014

(87) PCT Pub. No.: WO2013/180537
PCT Pub. Date: Dec. 5, 2013

(65) Prior Publication Data
US 2015/0126461 A1    May 7, 2015

(30) Foreign Application Priority Data

May 31, 2012    (KR) .................. 10-2012-0058752

(51) Int. Cl.
*A61K 47/48* (2006.01)
*C07K 14/43* (2006.01)
*C07K 14/435* (2006.01)
*C07K 7/08* (2006.01)
*A61K 38/00* (2006.01)

(52) U.S. Cl.
CPC .......... *A61K 47/48246* (2013.01); *C07K 7/08* (2013.01); *C07K 14/435* (2013.01); *A61K 38/00* (2013.01); *C07K 2319/00* (2013.01); *C07K 2319/10* (2013.01)

(58) Field of Classification Search
CPC ................... A61K 47/48246; C07K 14/435
See application file for complete search history.

(56) References Cited

U.S. PATENT DOCUMENTS 7,659,252 B2    2/2010 Wen et al.

FOREIGN PATENT DOCUMENTS

| KR | 10-2011-0004718 A | 1/2011 |
| KR | 10-2011-0049346 A | 5/2011 |
| WO | WO 2007/035474 A2 | 3/2007 |
| WO | WO 2009/005793 A2 | 1/2009 |
| WO | WO 2012/064429 A2 | 5/2012 |

OTHER PUBLICATIONS

Hsu, T., and Mitragotri, S., "Delivery of siRNA and other macromolecules into skin and cells using a peptide enhancer," *Proceedings of the National Academy of Sciences* 108(38): 15816-15821, National Academy of Sciences, United States (Sep. 20, 2011).
Noguchi, H. and Matsumoto, S., "Protein Transduction Technology: A Novel Therapeutic Perspective," *Acta Medica Okayama* 60(1):1-11, Okayama University Medical School, Japan (2006).
Lopes, L.B., et al., "Comparative Study of the Skin Penetration of Protein Transduction Domains and a Conjugated Peptide," *Pharmaceutical Research* 22(5):750-757, Kluwer Academic/Plenum Publishers, United States (2005).

*Primary Examiner* — Amber D Steele
(74) *Attorney, Agent, or Firm* — Sterne, Kessler, Goldstein & Fox P.L.L.C.

(57) ABSTRACT

The present invention relates to a skin-permeating peptide, and more particularly, the present invention relates to an isolated peptide capable of permeating the skin to deliver a drug to the skin, to an isolated polynucleotide coding the peptide, to a composition for transdermal delivery comprising the peptide, and to a peptide/cargo composite comprising the peptide and cargo.

10 Claims, 1 Drawing Sheet

SEQUENCE LISTING

<160> NUMBER OF SEQ ID NOS: 21

<210> SEQ ID NO 1
<211> LENGTH: 12
<212> TYPE: PRT
<213> ORGANISM: Artificial Sequence
<220> FEATURE:
<223> OTHER INFORMATION: S3-1

<400> SEQUENCE: 1

Asn Gln Thr Asp His Leu Phe Ser Thr Phe Ile Ser
1               5                   10

<210> SEQ ID NO 2
<211> LENGTH: 12

```
<212> TYPE: PRT
<213> ORGANISM: Artificial Sequence
<220> FEATURE:
<223> OTHER INFORMATION: S3-2

<400> SEQUENCE: 2

Asn Gly Ser Leu Asn Thr His Leu Ala Pro Ile Leu
1               5                   10

<210> SEQ ID NO 3
<211> LENGTH: 12
<212> TYPE: PRT
<213> ORGANISM: Artificial Sequence
<220> FEATURE:
<223> OTHER INFORMATION: S3-3

<400> SEQUENCE: 3

Gly Gly Ser Ile Ala Ala Ser Glu Leu Glu Tyr Tyr
1               5                   10

<210> SEQ ID NO 4
<211> LENGTH: 12
<212> TYPE: PRT
<213> ORGANISM: Artificial Sequence
<220> FEATURE:
<223> OTHER INFORMATION: S3-7

<400> SEQUENCE: 4

Glu Leu Lys Gln Val Val Ile Ser Asp Ile Asn His
1               5                   10

<210> SEQ ID NO 5
<211> LENGTH: 12
<212> TYPE: PRT
<213> ORGANISM: Artificial Sequence
<220> FEATURE:
<223> OTHER INFORMATION: S3-8

<400> SEQUENCE: 5

Met Val Arg Asp His Pro Gly Leu Ser Gly Trp Thr
1               5                   10

<210> SEQ ID NO 6
<211> LENGTH: 12
<212> TYPE: PRT
<213> ORGANISM: Artificial Sequence
<220> FEATURE:
<223> OTHER INFORMATION: S3-9

<400> SEQUENCE: 6

Thr Ser Gly Ile Ser Ile Asn Lys Leu Pro His Thr
1               5                   10

<210> SEQ ID NO 7
<211> LENGTH: 12
<212> TYPE: PRT
<213> ORGANISM: Artificial Sequence
<220> FEATURE:
<223> OTHER INFORMATION: S4-4

<400> SEQUENCE: 7

Ile Phe Ala Ala Leu Asp Tyr Asn Leu Gly Arg His
1               5                   10

<210> SEQ ID NO 8
<211> LENGTH: 12
<212> TYPE: PRT
```

```
<213> ORGANISM: Artificial Sequence
<220> FEATURE:
<223> OTHER INFORMATION: S4-7

<400> SEQUENCE: 8

Asp Met Lys Trp Thr Leu Lys Glu Trp Met Thr His
1               5                   10

<210> SEQ ID NO 9
<211> LENGTH: 12
<212> TYPE: PRT
<213> ORGANISM: Artificial Sequence
<220> FEATURE:
<223> OTHER INFORMATION: S4-9

<400> SEQUENCE: 9

Gln Ile Glu Lys His Val Tyr Phe Asn Ala Ser Gln
1               5                   10

<210> SEQ ID NO 10
<211> LENGTH: 12
<212> TYPE: PRT
<213> ORGANISM: Artificial Sequence
<220> FEATURE:
<223> OTHER INFORMATION: S4-10

<400> SEQUENCE: 10

Thr Asn Ile Pro Ser Leu Ser Gly Ile Leu Met Lys
1               5                   10

<210> SEQ ID NO 11
<211> LENGTH: 36
<212> TYPE: DNA
<213> ORGANISM: Artificial Sequence
<220> FEATURE:
<223> OTHER INFORMATION: S3-1

<400> SEQUENCE: 11
aatcagactg atcatctttt ttcgacgttt atttct                       36

<210> SEQ ID NO 12
<211> LENGTH: 36
<212> TYPE: DNA
<213> ORGANISM: Artificial Sequence
<220> FEATURE:
<223> OTHER INFORMATION: S3-2

<400> SEQUENCE: 12
aatggttctc ttaatactca tcttgcgccg attctg                       36

<210> SEQ ID NO 13
<211> LENGTH: 36
<212> TYPE: DNA
<213> ORGANISM: Artificial Sequence
<220> FEATURE:
<223> OTHER INFORMATION: S3-3

<400> SEQUENCE: 13
ggtggtagta ttgctgcttc ggagctggag tattat                       36

<210> SEQ ID NO 14
<211> LENGTH: 36
<212> TYPE: DNA
<213> ORGANISM: Artificial Sequence
<220> FEATURE:
<223> OTHER INFORMATION: S3-7
```

<400> SEQUENCE: 14
gagctgaagc aggttgtgat ttctgatatt aatcat                                 36

<210> SEQ ID NO 15
<211> LENGTH: 36
<212> TYPE: DNA
<213> ORGANISM: Artificial Sequence
<220> FEATURE:
<223> OTHER INFORMATION: S3-8

<400> SEQUENCE: 15
atggttcggg atcatcctgg tctttctggt tggacg                                 36

<210> SEQ ID NO 16
<211> LENGTH: 36
<212> TYPE: DNA
<213> ORGANISM: Artificial Sequence
<220> FEATURE:
<223> OTHER INFORMATION: S3-9

<400> SEQUENCE: 16
acttcgggga tttctattaa taagttgccg catact                                 36

<210> SEQ ID NO 17
<211> LENGTH: 36
<212> TYPE: DNA
<213> ORGANISM: Artificial Sequence
<220> FEATURE:
<223> OTHER INFORMATION: S4-4

<400> SEQUENCE: 17
atttttgctg cgttggatta taatctgggt cgtcat                                 36

<210> SEQ ID NO 18
<211> LENGTH: 36
<212> TYPE: DNA
<213> ORGANISM: Artificial Sequence
<220> FEATURE:
<223> OTHER INFORMATION: S4-7

<400> SEQUENCE: 18
gatatgaagt ggacgctgaa ggagtggatg actcat                                 36

<210> SEQ ID NO 19
<211> LENGTH: 36
<212> TYPE: DNA
<213> ORGANISM: Artificial Sequence
<220> FEATURE:
<223> OTHER INFORMATION: S4-9

<400> SEQUENCE: 19
cagattgaga agcatgttta ttttaatgct agtcag                                 36

<210> SEQ ID NO 20
<211> LENGTH: 36
<212> TYPE: DNA
<213> ORGANISM: Artificial Sequence
<220> FEATURE:
<223> OTHER INFORMATION: S4-10

<400> SEQUENCE: 20
acgaatattc cttcgttgtc ggggattctt atgaag                                 36

<210> SEQ ID NO 21
<211> LENGTH: 12

```
<212> TYPE: PRT
<213> ORGANISM: Artificial Sequence
<220> FEATURE:
<223> OTHER INFORMATION: Control

<400> SEQUENCE: 21

Thr Asp Met Asn Lys Thr Glu Ile Arg Phe Val Arg
1               5                   10
```

SKIN-PERMEATING PEPTIDE

TECHNICAL FIELD

The present invention relates to a skin permeable peptide, and more particularly, to an isolated peptide capable of permeating the skin to deliver a drug, an isolated polynucleotide encoding the peptide, a composition for transdermal delivery including the peptide, and a peptide-cargo complex including the peptide and a cargo.

BACKGROUND ART

Drug delivery through the skin has a variety of applications and forms such as analgesic patches, nicotine patches, or birth control patches, because of its convenience in use. Drug delivery through the skin mainly involves the delivery through the skin into systemic circulation, but drugs such as therapeutic agents for atopic dermatitis, cosmetics for whitening or wrinkle improvement, etc. are used for the transport of drugs into the skin organ itself. Despite the convenience and functionality, there are many difficulties in drug delivery through the skin, due to the skin structure. Thus, it is difficult to develop drugs permeating the skin. The outermost layer of skin has a cornified layer which is composed of about 10 to 15 layers of corneocytes having a thickness of about 10 μm to 45 μm, and this cornified layer has the form called the "brick and mortar" structure. In the cornified layer, the brick structure is composed of corneocytes containing abundant keratin, and the mortar structure is composed of lipids such as ceramide, fatty acid, or wax which fill the space between corneocytes. This structure prevents loss of internal moisture from skin surface and external attacks. However, this structure has the property of very low permeability as faithfully corresponding to its functions. Only molecules having low molecular weight of 500 Da or less can pass through the skin by diffusion, mainly, through the intracellular lipid layer of the mortar structure, or the hydrophilic structure between lipid layers. Such drug delivery through the skin can be greatly influenced by the properties of the drug. Drug delivery through the skin may also occur through the structures such as sweat glands, skin pores, sebaceous glands, in addition to the direct passage through the skin surface.

Under this background, many studies have been actively conducted, to develop drugs which cap pass through the skin to be uniformly distributed throughout the skin regardless of size or property of the molecule, and drug delivery methods. For example, Korean Patent No. 1054519 discloses a human growth hormone-derived peptide which is more excellent in stability and skin permeability than the natural human growth hormones, and a composition including the same. Korean Patent No. 1104223 discloses an IL-10 derived peptide which has the same functions as human IL-10 (interleukin-10) and is more excellent in stability and skin permeability than the natural IL-10, and a composition including the same. However, since these peptides themselves exhibit functionality, there is a disadvantage that they cannot be used as a carrier for drug delivery. Therefore, a skin permeable peptide which can be used in the treatment of skin diseases and enhancement of skin permeability of pharmaceutically active compositions has been developed (U.S. Pat. No. 7,659,252). This peptide is advantageous in that it exhibits excellent skin permeability and can be also used as a carrier for transdermal delivery of other drugs. However, this peptide, once it passes through the skin, is consumed through the circulation system in the body, and thus drugs for targeting the skin cannot exhibit their specific effects.

Under this background, the present inventors have made strenuous efforts to develop a skin permeable peptide which can be used as a carrier for transdermal delivery of drugs and also has the property of remaining in the skin, and as a result, they have developed an isolated peptide having any one amino acid sequence of SEQ ID NOs. 1 to 10, thereby completing the present invention.

DISCLOSURE

Technical Problem

An object of the present invention is to provide an isolated peptide which consists of any one amino acid sequence selected from the group consisting of SEQ ID NOs. 1 to 10.

Another object of the present invention is to provide an isolated polynucleotide encoding the peptide.

Still another object of the present invention is to provide a peptide-cargo complex comprising the isolated peptide and a cargo.

Still another object of the present invention is to provide a composition for transdermal delivery, comprising the isolated peptide.

Still another object of the present invention is to provide a method for transdermal delivery of the cargo using the peptide.

Technical Solution

In one aspect, the present invention provides an isolated peptide which consists of any one amino acid sequence selected from the group consisting of SEQ ID NOs. 1 to 10.

Abbreviations of the amino acid sequences used herein are in accordance with the IUPAC-IUB nomenclature as follows.

| Alanine | A | Arginine | R |
|---|---|---|---|
| Asparagine | N | Aspartic acid | D |
| Cysteine | C | Glutamic acid | E |
| Glutamine | Q | Glycine | G |
| Histidine | H | Isoleucine | I |
| Leucine | L | Lysine | K |
| Methionine | M | Phenylalanine | F |
| Proline | P | Serine | S |
| Threonine | T | Tryptophan | W |
| Tyrosine | Y | Valine | V |

In the present invention, developed was a novel peptide which exhibits skin permeability and additionally skin retention and thus can be applied to transdermal delivery systems for drugs such as peptides or proteins.

The peptide of the present invention may consist of any one amino acid sequence of the following SEQ ID NOs. 1 to 10:

```
                                        (SEQ ID NO. 1)
            NQTDHLFSTFIS, (SEQ ID NO. 2)
            NGSLNTHLAPIL, (SEQ ID NO. 3)
            GGSIAASELEYY,
```

```
                                                    (SEQ ID NO. 4)
ELKQVVISDINH, (SEQ ID NO. 5)
MVRDHPGLSGWT, (SEQ ID NO. 6)
TSGISINKLPHT, (SEQ ID NO. 7)
IFAALDYNLGRH, (SEQ ID NO. 8)
DMKWTLKEWMTH, (SEQ ID NO. 9)
QIEKHVYFNASQ, (SEQ ID NO. 10)
TNIPSLSGILMK.
```

In the present invention, the isolated peptide having an amino acid sequence which is prepared by removing or substituting one or more amino acids at the end of the above sequence or which shows 80% or more homology therewith may be also included in the scope of the present invention, as long as it consists of any one sequence of SEQ ID NOs, 1 to 10 and also exhibits skin permeability or/and skin retention.

The isolated peptide consisting of any one amino acid sequence of SEQ ID NOs. 1 to 10 of the present, invention is characterized in that it exhibits skin permeability, and additionally, skin retention.

As used herein, the term "skin permeability" means the peptide's ability to pass through the skin to permeate into the skin, and the term "skin retention" means the peptide's ability that the peptide permeating the skin passes through the skin tissue, and then is not delivered to the circulation system, but binds to the tissue of the skin to remain in the skin. In a pharmaceutical composition or a cosmetic targeting the skin tissue, the property of remaining in the skin tissue so that, the component binding to the peptide exerts its function in the skin tissue or skin cell is preferred. Therefore, since the peptide of the present invention is excellent in skin retention as well as in skin permeability, it can be useful as a carrier of a pharmaceutical composition or a cosmetic targeting the skin tissue.

The peptide showing skin permeability can be used for transdermal delivery of a variety of cargos binding thereto, such as other peptides, proteins, polynucleotides, oligonucleotides, siRNA or commercially available drugs.

As used herein, the term "cargo" means a substance that passes through the skin to be delivered into the skin. With, respect to the objects of the present invention, the type of the cargo is not particularly limited, as long as it is linked to the isolated peptide of the present invention to be delivered into the skin, and examples thereof include a substance for gene therapy such as a peptide, a protein, a polynucleotide, an oligonucleotide, a ribozyme, siRNA, a vector or a virus, or for a commercially available drug, etc. In one embodiment of the present invention, it was found that a phage presenting the peptide of the present invention by a phage display method is able to permeate the porcine skin (Examples 1 to 5).

The cargo may be delivered into the skin in the form of a complex which is prepared by linking the isolated peptide of the present invention thereto. Herein, in the complex, the cargo may be linked to the peptide via a covalent bond; or the cargo may be linked to the peptide via a non-covalent interaction. Further, if the cargo is a peptide or a protein, it may be in the form of a fusion protein, but is not limited thereto.

If the cargo is linked to the peptide via a covalent bond, they may be linked to each other via a linker or directly.

As used herein, the term "linker" basically refers to a means capable of linking two different fusion partners (e.g., biological polymers, etc.) using a covalent bond. The linker may be a peptide linker or a non-peptide linker. If the linker is a peptide linker, it may be composed of one or more amino acids.

The peptide comprising any one amino acid sequence selected from the group consisting of SEQ ID NOs. 1 to 10 of the present invention may be in the form of a modified peptide, of which N- or/and C-terminal is modified chemically or protected with organic compounds, or of which terminal is added with amino acids, for protection against proteolytic enzymes and for improvement of its stability. Particularly, if the peptide is chemically synthesized, its N- and C-terminal are electrically charged. In order to remove the charge, the N-terminal acetylation or/and C-terminal amidation may be performed, but is not particularly limited thereto. In addition, the peptide may be a peptide, of which C-terminal is further linked with a dansyl group, but is not limited thereto.

Depending on its length, the peptide of the present invention may be synthesized by a method, well known, in the art, for example, by an automated peptide synthesizer, or produced by a genetic engineering technology. For example, a fusion gene encoding a fusion protein including a fusion partner and the peptide of the present invention, is prepared by genetic engineering, and then transformed into a host cell to express the fusion protein. Thereafter, the peptide of the present invention is cleaved and isolated from the fusion protein using a protease or a compound so as to produce the desired peptide. To this end, a DNA sequence encoding amino acid residues which can be cleaved by a protease such as Factor Xa or enterokinase, or a compound such as CNBr or hydroxylamine may be inserted between the polynucleotides encoding the fusion partner and the peptide of the present invention.

According to one embodiment of the present invention, 10 types of skin permeable peptides (SEQ ID NOs. 1 to 10) were selected by a phage display method, and skin permeability of the phages including the selected skin permeable peptides were examined. As a result, they showed excellent skin permeability, compared to a control group (Table 1). In addition, peptide derivatives, each C-terminal was linked with a dansyl group, were synthesized, and their absorbance was measured to examine skin permeability of the peptides. As a result, these peptides also showed excellent skin permeability (Table 2). Furthermore, the skin retention of the phages including the skin permeable peptides was examined. As a result, they showed remarkably excellent skin retention, compared to the control group (Table 3). In addition, skin retention of the peptides was examined using derivatives, each derivative prepared by linking the C-terminal of the peptide with a dansyl group. As a result, the peptides showed excellent skin retention (Table 4).

In another aspect, the present invention provides a polynucleotide encoding the peptide. In this regard, the polynucleotide encoding the peptide of the present invention may preferably consist of any one nucleotide sequence of the following SEQ ID NOs. 11 to 20 due to codon degeneracy, but is not particularly limited thereto.

Skin permeable peptide-encoding polynucleotides:

```
                                        (SEQ ID NO. 11)
AATCAGACTGATCATCTTTTTTCGACGTTTATTTCT, (SEQ ID NO. 12)
AATGGTTCTCTTAATACTCATCTTGCGCCGATTCTG, (SEQ ID NO. 13)
GGTGGTAGTATTGCTGCTTCGGAGCTGGAGTATTAT, (SEQ ID NO. 14)
GAGCTGAAGCAGGTTGTGATTTCTGATATTAATCAT, (SEQ ID NO. 15)
ATGGTTCGGGATCATCCTGGTCTTTCTGGTTGGACG, (SEQ ID NO. 16)
ACTTCGGGGATTTCTATTAATAAGTTGCCGCATACT, (SEQ ID NO. 17)
ATTTTTGCTGCGTTGGATTATAATCTGGGTCGTCAT, (SEQ ID NO. 18)
GATATGAAGTGGACGCTGAAGGAGTGGATGACTCAT, (SEQ ID NO. 19)
CAGATTGAGAAGCATGTTTATTTTAATGCTAGTCAG, (SEQ ID NO. 20)
ACGAATATTCCTTCGTTGTCGGGGATTCTTATGAAG
```

In still another aspect, the present invention provides a peptide-cargo complex comprising the isolated peptide and the cargo.

The isolated peptide, cargo and complex are the same as described above.

In still another aspect, the present invention provides a composition for transdermal delivery, comprising the isolated peptide.

The composition may further include the cargo. If the composition comprises the cargo, the peptide and the cargo may exist in the form of the peptide-cargo complex.

Since the peptide shows skin permeability, it can be used as a composition for transdermal or percutaneous delivery of a variety of cargos such as a peptide, a protein, a polynucleotide, an oligonucleotide, a ribozyrae, siRNA or a commercially available drug, etc., and it functions as a carrier of the cargo. The carrier refers to a means for delivering a substance to a particular site. The peptide of the present invention exhibits skin permeability, and thus the composition including the same can be used as a carrier for delivering the cargo into the skin.

In particular, to deliver a drug through the body surface, the carrier or the composition may include (a) a sufficient amount of the peptide of the present invention, which causes drug delivery through the body surface without damage to the body; and (b) an effective amount of the cargo, but is not limited thereto.

In view of the objects, the composition for transdermal delivery comprising the peptide of the present invention may be preferably formulated into a preparation which is convenient for delivery to the skin, for example, in the form of an external preparation for skin. The composition may be also prepared together with liposomes, micelles, and microspheres.

As used herein, the term "external preparation for skin" means a preparation provided for external use. Examples thereof include an ointment, a cream, a gel, a lotion, a paste, a patch, etc., but the type thereof is not particularly limited, as long as it is intended to deliver a desired substance into the skin when applied to the surface of the skin.

In addition, the composition may comprise one or more pharmaceutically acceptable carriers or additives known in the art. Herein, the carrier is preferably a substance which is suitable for transdermal delivery or topical delivery. Further, the carrier or additive useful in the present invention is preferably those which are not toxic to the skin and do not adversely interact with other components included in the composition.

Furthermore, the composition of the present invention can be used for delivering a drug which is not easily delivered as it is to the skin, and thus it may further include a substance capable of enhancing skin permeation, in addition to the peptide of the present invention. The substance for enhancing skin permeation is preferably a substance capable of minimizing skin damage, irritation and systemic symptoms. Examples of the substance capable of enhancing skin permeation, which can be further included in the composition of the present invention, include saturated or unsaturated fatty acids; aliphatic alcohols; bile acids; non-ionic surfactants, amine, amide, hydrocarbon solvents, terpenes, lower alkyl esters, cyclodextrin enhancers, nitrogen-containing heterocycles, sulfoxides, and urea; and derivatives thereof, but are not limited thereto.

Further, the composition including the peptide of the present invention may be in the form of a pharmaceutical composition, if the substance to be delivered is a therapeutic substance.

When the peptide of the present invention is formulated into a pharmaceutical composition, it may be prepared using diluents or excipients ordinarily employed, such as a filler, an extender, a binder, a wetting agent, a disintegrating agent, a surfactant, etc. It may include an aseptic aqueous solution, a non-aqueous solvent, a suspension, an emulsion, a lyophilized agent, and suppository. For the non-aqueous solvent and suspension, propylene glycol, polyethylene glycol, plant oil such as olive oil, injectable ester such as ethyloleate may be used. As a suppository base, witepsol, macrogol, tween 61, cacao butter, lauric butter, glycerogelatin or the like may be used.

Further, the peptide of the present invention may include carbohydrates such as glucose, sucrose, or dextran, antioxidants such as ascorbic acid or glutathione, chelating agents, low molecular weight proteins, or other stabilizers in order to increase the stability or the absorption.

Further, the composition may be in the form of a cosmetic composition.

Since the peptide exhibits excellent skin permeability and also skin retention, it is included in a cosmetic composition to help deliver an active ingredient in the cosmetic composition, for example, various components such as a whitening ingredient, into the skin.

The cosmetic composition of the present invention may be used as a component of general cosmetics or cosmeceuticais, together with a supplementary agent commonly used in the field of cosmetology, for example, a lipid, an organic solvent, a solubilizer, a concentrator, a gelation agent, a softener, an antioxidant, a suspending agent, a stabilizer, a foaming agent, an aromatic, a surfactant, water, an ionic or non-ionic emulsifier, a filler, a sequestrant, a chelating agent, a preservative, a vitamin, a blocker, a wetting agent, an essential oil, a dye, a pigment, a hydrophilic or lipophilic activator, a lipid vesicle, or other supplementary agents commonly used in the field of cosmetology or dermatology such as other components typically used in cosmetics.

As used herein, the term "cosmeceutical (cosmedical)" refers to a functional product which is prepared by introducing a cosmetic with a specialized therapeutic function of a medicine so as to have the specialized function by enhancing a physiological efficacy or effect, unlike the general cosmetics. For example, the cosmeceutical means a product to help skin whitening, a product to help improve skin wrinkle, a product to help sun tanning or help protect the skin from UV.

The cosmetic including the cosmetic composition of the present invention may be formulated in the form of, for example, a solution, a suspension, an emulsion, a paste, a gel, a cream, a lotion, a powder, a soap, a surfactant-containing cleanser, an oil, a powder foundation, an emulsion foundation, a wax foundation or a spray, but is not limited thereto. In more detail, it may be formulated in the form of a skin softener, an astringent lotion, a nutrient lotion, a nutrient cream, a massage cream, a lotion, a gel, an essence, an eye cream, a cleansing cream, a cleansing foam, a cleansing water, a pack, an ointment, a stick, a patch, a spray or powder.

In still another aspect, the present invention provides a method for transdermal delivery of the cargo using the peptide.

The peptide and the cargo are the same as described above.

In detail, the method for transdermal delivery of the cargo of the present invention may be a method including the step of applying an effective amount of the peptide-drug complex or the composition including the same to the skin of a subject. Since the peptide of the present invention exhibits excellent skin permeability, the cargo linked to the peptide can be effectively delivered into the skin by using the method. The subject may be any one without limitation, as long as it is in need of transdermal delivery of the cargo. Example thereof includes a mammal or a bird such as cow, pig, sheep, chicken, dog, human, etc., but is not limited thereto.

Advantageous Effects

The peptide of the present invention exhibits excellent skin retention as well as skin permeability, and therefore, it can be widely used in the development of a variety of agents for transdermal delivery which are intended to be applied to the skin tissue.

BEST MODE

Figure 1:
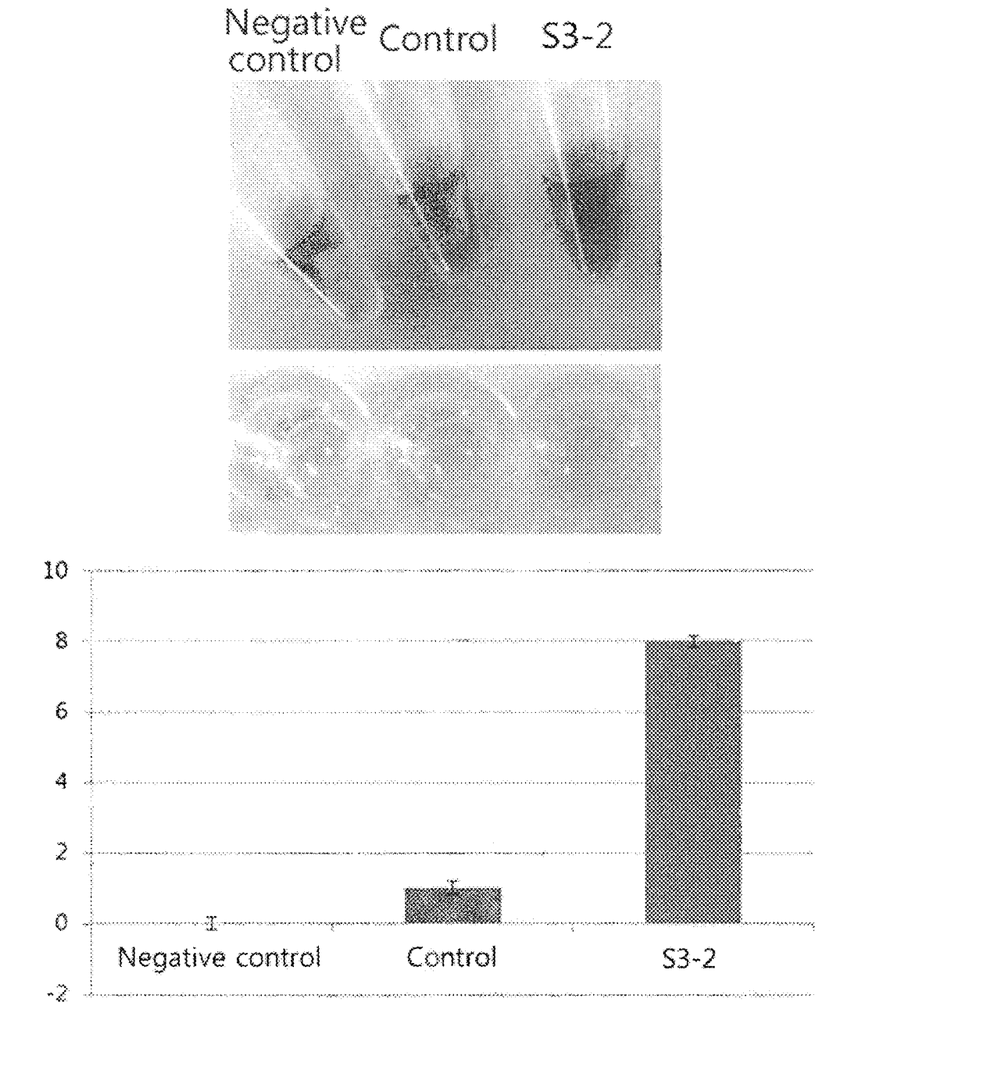
The FIGURE is an image and a graph showing the amount of each phage expressing the negative control group, the control group, or S3-2 which bound to the porcine skin.

Hereinafter, the present invention will be described in more detail with reference to Examples. However, these Examples are for illustrative purposes only, and the invention is not intended to be limited by these Examples.

Example 1

Selection of Skin Permeable Peptide

To select skin permeable peptides, a transdermal diffusion test was applied. To this end, Franz glass cell (Standard diameter 9 mm, Receiver 5 ml, Permgear) was used. The porcine skin (0.7 mm in thickness, Medikinetics) was placed between the top and bottom of the glass cell, and the top was treated with phages. Then, the phages that penetrated the porcine skin to remain in the receiver at the bottom were amplified. This procedure was conducted once, which was defined as 1 round of selection. The phages amplified from round 1 were subjected to round 2. In this manner, phages showing excellent skin permeability were selected competitively, and total 3 rounds of selection were performed.

Further, to reduce a non-specific binding which may occur between the skin and the coat protein of the phage, 1% BSA (Sigma) dissolved in 500 µl and 5 ml of TBS (50 mM Tris pH 7.5, 150 mM NaCl) solution was used on the top and bottom of the glass cell, respectively.

Furthermore, to begin the experiment using phages having random peptide sequences, a Ph.D-12 phage library kit (New England Biolab) was used. $10^9$ phages were treated to 500 µl of TBS (1% BSA), followed by incubation for 16 hours. All 5 ml of TBS in the receiver was used to amplify the phage.

As a host cell for phage amplification, E. coli ER2738 (New England Biolab) was used. ER2738 cultured with shaking was seeded in 25 ml of LB medium, and then treated with 5 ml of TBS containing phages which penetrated at O.D. (550 nm) of 0.5, followed by incubation for 4 hours. Thereafter, cells were centrifuged at 8000 G to separate the phages from E. coli. Next, 6 ml of precipitate solution (20% PEG6000, 2.5 M NaCl) was treated to the supernatant containing the phage to precipitate the phages. After centrifugation at 8000 G, the precipitated phages were treated with TBS solution to separate and store the phages.

Finally, to confirm the peptides of the skin permeable phages, the phages were amplified in single colonies, E. coli ER2738 having phages was selected by blue color on a LB/X-gal/IPTG plate. In detail, a proper amount of phages were diluted in TBS, and 2 µl thereof was treated to 300 µl of ER2738 culture broth, and then the broth was mixed with 4 ml of TOP agar, and treated to the top of the LB/X-gal/IPTG plate. The plate was incubated for 16 hours, and then blue colonies were selected. Each colony was cultured in 5 ml of ER2738 culture broth for 6 hours, and then DNA was isolated using a Ph.D-13 phage spin kit (Qiagen). Nucleotide sequences thereof were analyzed to select 10 types of skin permeable peptides (S3-1 phage (SEQ ID NO. 1), S3-2 phage (SEQ ID NO. 2), S3-3 phage (SEQ ID NO. 3), S3-7 phage (SEQ ID NO. 4), S3-8 phage (SEQ ID NO. 5), S3-9 phage (SEQ ID NO. 6), S4-4 phage (SEQ ID NO. 7), S4-7 phage (SEQ ID NO. 8), S4-9 phage (SEQ ID NO. 9), and S4-10 phage (SEQ ID NO. 10)).

Example 2

Skin Permeability Test of Phage Including Skin Permeable Peptide

Skin permeability of the phage capable of expressing each of the peptides having amino acid sequences of SEQ ID NOs. 1 to 10 which were selected in Example 1 was examined.

In detail, the porcine skin was placed between the top and bottom of Franz glass cell. To reduce a non-specific binding which may occur between the skin and the coat protein of the phage, 1% BSA dissolved in 500 µl and 5 ml of TBS solution was used on the top and bottom of the glass cell, respectively. The number of phage to be treated was determined as $10^{10}$, and then treated to the top of Franz glass cell. At this time, a phage capable of expressing the peptide having the amino acid sequence of "TDMNKTEIRFVR (SEQ ID NO. 21)" was used as a control group. This phage was reacted with the porcine skin for 16 hours, and then the number of phage that penetrated the porcine skin to remain in the receiver was measured. To this end, 300 μl of ER2738 culture broth was mixed with 10 μl of TBS of the receiver containing phage, and then the resultant was mixed with 4 ml of TOP agar. The mixture was treated to the top of the LB/X-gal/IPTG plate, and the plate was incubated for 16 hours. Then, the number of blue colonies was counted (Table 1).

TABLE 1

Number of porcine skin-permeating phage

| Type of phage | Number of permeating phage |
|---|---|
| Control group | 3 |
| S3-1 | 3100 |
| S3-2 | 9000 |
| S3-3 | 2500 |
| S3-7 | 1400 |
| S3-8 | 250 |
| S3-9 | 360 |
| S4-4 | 440 |
| S4-7 | 720 |
| S4-9 | 450 |
| S4-10 | 350 |

As shown in Table 1, all the phages having 10 types of the peptides thus selected showed excellent skin permeability, compared to the control group. In particular, it was found that S3-1, S3-2, S3-3 and S3-7 showed more excellent skin permeability among the phages having 10 types of the peptides, and of them, S3-2 showed the most excellent skin permeability.

These results indicate that 10 types of the isolated peptides of the present invention have excellent skin permeability.

Example 3

Skin Permeability Test of Skin Permeable Peptide Derivative

A dansyl group was linked at the C-terminus of each peptide having any one amino acid sequence of SEQ ID NOs. 1 to 10 which were selected in Example 1 so as to synthesize a derivative thereof, and it was intended to examine skin permeability thereof.

In detail, each of the peptides was chemically synthesized, and then a dansyl group was added at the C-terminus of each peptide to synthesize a derivative thereof. As a control group, a peptide composed of the amino acid sequence of "TDMNKTEIRFVR (SEQ ID NO. 21)" which was prepared by adding a dansyl group at the C-terminus was used.

Further, the porcine skin was placed between the top and bottom of Franz glass cell, and 500 μl and 5 ml of TBS solution were added to the top and bottom of the cell, respectively. Then, each derivative was added at the same concentration to the top of the cell, followed by incubation for 16 hours. After completion of the incubation, the amount of each derivative in the receiver at the bottom was measured using a victor fluorescence meter (340/520) to compare permeation degree (Table 2),

TABLE 2

Amount of porcine skin-permeating peptide derivative

| Type of derivative | Fluorescence intensity (340/520) |
|---|---|
| Control group | 1500 |
| S3-1 peptide derivative | 42000 |
| S3-2 peptide derivative | 70000 |
| S3-3 peptide derivative | 19000 |
| S3-7 peptide derivative | 25000 |
| S3-8 peptide derivative | 22000 |
| S3-9 peptide derivative | 18000 |
| S4-4 peptide derivative | 4400 |
| S4-7 peptide derivative | 8600 |
| S4-9 peptide derivative | 16000 |
| S4-10 peptide derivative | 9000 |

As shown in Table 2, 10 types of the peptide derivatives thus synthesized showed very excellent skin permeability, compared to the control group. In particular, it was found that S3-1 peptide, S3-2 peptide, S3-3 peptide, S3-7 peptide, S3-8 peptide, S3-9 peptide and S4-9 peptide showed relatively excellent skin permeability among 10 types of the peptides, and of them, S3-2 peptide showed the most excellent skin permeability.

Example 4

Skin Retention Test of Phage Including Skin Permeable Peptide

Skin permeation mainly occurs by the mechanism of a diffusion of a substance dissolved in the components of the skin from the outermost layer to the innermost layers. Through this mechanism, an active ingredient can be effectively delivered throughout the skin. The skin surface is composed of corneocytes and intercellular materials. For effective skin permeation of the selected peptides, they should exhibit good solubility in the components constituting the skin surface. Such solubility of a substance in the skin components can be analyzed by measuring the amount of the substance which binds to the skin after reaction with the skin for a short time (10 minutes). In addition, when a wash-off product is used, it should exhibit high binding affinity to the skin. In this case, the product first binds to the skin, and then diffuses into the inner layer. Therefore, binding affinity of the selected phages to the skin was measured to examine the superiority of the peptides.

First, the porcine skin was cut into a size of 10 mm×10 mm, and then the phage capable of expressing each of the peptides which were selected in Examples was added thereto to measure their binding affinity to the porcine skin. At this time, a phage expressing the peptide having the amino acid sequence of "TDMNKTEIRFVR (SEQ ID NO. 21)" was used as a control group.

To measure the amount of the phage binding to the porcine skin, anti-M13 antibody-HRP conjugate was used. To remove signals due to binding of the antibody itself and the skin, a phage-free control group was determined as a negative control group. The porcine skin thus cut was put in a 1.5 ml tube, and 500 μl of TBS (1% BSA) was added thereto. Then, no phage was added to the negative control, and $10^{10}$ phages were added to the control group and the phage groups to be measured, followed by incubation for 10 minutes. Thereafter, they were washed using 1% BSA-containing TBS solution at 12,000 RPM for 1 minute 10 times. Subsequently, 500 μl of TBS solution containing anti-M13 antibody-HRP (Horseradish peroxidase) conjugate-containing 1% BSA was added, followed by incubation for 5 minutes. TBS solution containing 1% BSA was added to the culture, followed by washing at 12,000 RPM for 1 minute 10 times. The residual buffer was completely removed, and TMB solution (Tetramethylbenzidine solution, Amersham) was further added. At this time, TMB was degraded by HRP conjugated to the antibody to produce a blue color. Finally, 0.2 N sulfuric acid was added, to terminate the reaction, which changed the blue color to yellow. Then, absorbance (450 nm) was measured to determine binding affinity between phage-skin. Next, based on the absorbance which was obtained by deleting absorbance of the negative control group from each absorbance, each activity was compared and the results are shown in Table 3 and the FIGURE. The FIGURE is an image and a graph showing the amount of each phage expressing the negative control group, the control, group, or S3-2 which bound to the porcine skin.

TABLE 3

Amount of phage remaining in skin

| Type of phage | Absorbance (450 nm) |
|---|---|
| Control group | 0.07 |
| S3-1 | 0.32 |
| S3-2 | 0.56 |
| S3-3 | 0.25 |
| S3-7 | 0.27 |
| S3-8 | 0.21 |
| S3-9 | 0.18 |
| S4-4 | 0.21 |
| S4-7 | 0.22 |
| S4-9 | 0.21 |
| S4-10 | 0.21 |

As shown in Table 3 and the FIGURE, each of the peptides remaining in the skin showed high skin retention, compared to the control group. In particular, it was found that S3-1, S3-2, S3-3 and S3-7 showed relatively high skin binding affinity among 10 types of the peptides, and of them, S3-2 peptide showed the highest skin binding affinity.

Example 5

Skin Retention Test of Skin Permeable Peptide Derivative

To examine skin binding affinity of the derivatives synthesized in Example 3, the porcine skin was reacted with each of the derivatives, and the amount of the peptide dissolved in the surface was measured. In detail, the porcine skin was cut and put in a 1.5 ml tube, and 500 μl of TBS (1% BSA) was added thereto. The control group and each of the derivates to be measured were added thereto, followed by incubation with the skin for 10 minutes. As a control group, the peptide having the amino acid sequence of "TDMNK-TEIRFVR (SEQ ID NO. 21)" was used. After incubation, washing was performed using TBS (1% BSA) at 12,000 RPM for 1 minute ten times, and the porcine skin in which the reaction was completed was transferred to a 24-well plate. The amount of the peptide remaining on the surface was measured using a victor fluorescence meter (340/520) and compared (Table 4).

TABLE 4

Amount of peptide derivative remaining in porcine skin

| Type of derivative | Fluorescent intensity (340/520) |
|---|---|
| control group | 4200 |
| S3-1 peptide derivative | 143000 |
| S3-2 peptide derivative | 260000 |
| S3-3 peptide derivative | 47000 |
| S3-7 peptide derivative | 98000 |
| S3-8 peptide derivative | 100000 |
| S3-9 peptide derivative | 47000 |
| S4-4 peptide derivative | 13200 |
| S4-7 peptide derivative | 37600 |
| S4-9 peptide derivative | 56000 |
| S4-10 peptide derivative | 25000 |

As shown in Table 4, the level of each peptide derivative remaining in the skin was higher than that of the control group, in particular, it was found that S3-1 peptide, S3-2 peptide, S3-7 peptide and S3-8 peptide regained in the skin at a relatively high level, among 10 types of the peptides, and of them, S3-2 peptide remained in the skin at the highest level.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

The invention claimed is:

1. An isolated peptide which consists of any one amino acid sequence selected from the group consisting of SEQ ID NOs: 1 to 10.

2. The peptide according to claim 1, wherein the peptide is amidated at its C-terminus.

3. An isolated nucleic acid molecule comprising a polynucleotide sequence encoding the peptide of claim 1.

4. The nucleic acid molecule according to claim 3, comprising a nucleotide sequence selected from the group consisting of SEQ ID NOs: 11 to 20.

5. A composition for transdermal delivery, comprising the isolated peptide of claim 1.

6. The composition according to claim 5, further comprising a cargo.

7. The composition according to claim 6, wherein the cargo is linked to the isolated peptide via a covalent bond; or the cargo is linked to the isolated peptide via a non-covalent interaction.

8. The composition according to claim 5, wherein the composition is in the form of an external preparation for skin.

9. A peptide-cargo complex, comprising the isolated peptide of claim 1 and a cargo.

10. A method for transdermal delivery of a cargo, comprising applying an effective amount of the peptide-cargo complex of claim 9 or a composition comprising the same to the skin of a subject.

* * * * *

UNITED STATES PATENT AND TRADEMARK OFFICE
CERTIFICATE OF CORRECTION

PATENT NO. : 9,687,560 B2  
APPLICATION NO. : 14/404928  
DATED : June 27, 2017  
INVENTOR(S) : Seol Hoon Lee Page 1 of 1

It is certified that error appears in the above-identified patent and that said Letters Patent is hereby corrected as shown below:

In the Claims

In Column 19, Claim 1, Line 13, "which consists of any one" should be replaced with --comprising an--.

Signed and Sealed this  
Tenth Day of October, 2017

Joseph Matal  
*Performing the Functions and Duties of the*  
*Under Secretary of Commerce for Intellectual Property and*  
*Director of the United States Patent and Trademark Office*